United States Patent
Bindschedler et al.

(10) Patent No.: US 11,180,605 B2
(45) Date of Patent: *Nov. 23, 2021

(54) RIGID FOAM COMPRISING A POLYESTER POLYOL

(71) Applicants: TEREOS STARCH & SWEETENERS BELGIUM, Aalst (BE); CENTRE NATIONAL DE LA RECHERCHE SCIENTIFIQUE, Paris (FR); SOCIÉTÉ SOPREMA SAS, Strasbourg (FR); UNIVERSITÉ DE STRASBOURG, Strasbourg (FR)

(72) Inventors: Pierre Etienne Bindschedler, Strasbourg (FR); Alexandru Sarbu, Strasbourg (FR); Stephanie Laurichesse, Strasbourg (FR); Remi Perrin, Strasbourg (FR); Pierre Furtwengler, Paris (RE); Luc Avérous, Paris (FR); Andreas Redl, Aalst (BE)

(73) Assignees: TEREOS STARCH & SWEETENERS BELGIUM, Aalst (BE); CENTRE NATIONAL DE LA RECHERCHE SCIENTIFIQUE, Paris (FR); SOCIÉTÉSOPREMA SAS, Strasbourg (FR); UNIVERSITÉDE STRASBOURG, Strasbourg (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/327,523

(22) PCT Filed: Aug. 24, 2017

(86) PCT No.: PCT/IB2017/055110
§ 371 (c)(1),
(2) Date: Feb. 22, 2019

(87) PCT Pub. No.: WO2018/037373
PCT Pub. Date: Mar. 1, 2018

(65) Prior Publication Data
US 2019/0194379 A1  Jun. 27, 2019

(30) Foreign Application Priority Data
Aug. 24, 2016 (FR) ..................... 16/01253

(51) Int. Cl.
*C08G 18/42* (2006.01)
*C07C 67/08* (2006.01)
*C07C 69/40* (2006.01)
*C07C 69/44* (2006.01)
*C08G 63/668* (2006.01)
*C08K 5/00* (2006.01)
*C08J 9/12* (2006.01)
*C09D 175/04* (2006.01)
*C09J 175/04* (2006.01)
*C08G 18/76* (2006.01)
*C08G 63/672* (2006.01)
*E04B 1/74* (2006.01)

(52) U.S. Cl.
CPC .............. *C08G 18/42* (2013.01); *C07C 67/08* (2013.01); *C07C 69/40* (2013.01); *C07C 69/44* (2013.01); *C08G 18/4244* (2013.01); *C08G 18/7671* (2013.01); *C08G 63/668* (2013.01); *C08G 63/672* (2013.01); *C08J 9/125* (2013.01); *C08K 5/005* (2013.01); *C08K 5/0066* (2013.01); *C09D 175/04* (2013.01); *C09J 175/04* (2013.01); *C08G 2110/0008* (2021.01); *C08G 2110/0016* (2021.01); *C08G 2110/0025* (2021.01); *C08J 2375/04* (2013.01); *E04B 1/74* (2013.01)

(58) Field of Classification Search
CPC ......... C07C 67/08; C07C 69/40; C07C 69/44; C08G 18/42; C08G 18/4244; C08G 63/668; C08G 63/672; C08G 2101/0008; C08G 2101/0016; C08G 2101/0025; C08J 9/125; C08J 2375/04; C08K 5/005; C08K 5/0066; C09D 175/04; C09J 175/04; E04B 1/74
See application file for complete search history.

(56) References Cited

U.S. PATENT DOCUMENTS

| 2,863,855 A | 12/1958 | Wilson et al. |
| 2,980,650 A | 4/1961 | Wilson et al. |
| 4,001,180 A | 1/1977 | Doyle et al. |
| 4,404,295 A | 9/1983 | Carl et al. |
| 5,057,546 A | 10/1991 | Sudan |
| 5,605,940 A * | 2/1997 | Skowronski ............... B32B 5/18 521/172 |
| 2006/0084709 A1* | 4/2006 | Dobransky ........ C08G 18/4018 521/131 |

(Continued)

OTHER PUBLICATIONS

International Search Report dated Oct. 17, 2017 in corresponding International application No. PCT/IB2017/055110; 5 pages.

(Continued)

*Primary Examiner* — John M Cooney
(74) *Attorney, Agent, or Firm* — Maier & Maier, PLLC

(57) ABSTRACT

A rigid foam or a composition allowing a rigid foam to be obtained, including a polyester polyol or a polymer including a polyester polyol, the polyester polyol being obtained by a first polycondensation (a) of a C3 to C8 sugar alcohol Z and two identical or different C4 to C36 diacids Y and Y' and a second polycondensation (b) of the product obtained in (a) with two identical or different C2 to C12 diols X and X'.

18 Claims, 3 Drawing Sheets

(56) References Cited

U.S. PATENT DOCUMENTS

2015/0218415 A1\* 8/2015 Nixon ............... C08G 18/4288
524/590
2015/0299373 A1 10/2015 Nefzger et al.

OTHER PUBLICATIONS

Gustini, L. et al., "Enzymatic synthesis and preliminary evaluation as coating of sorbitol-based, hydroxy-functional polyesters with controlled molecular weights," European Polymer Journal, vol. 67, 2015, pp. 459-475.
Gustini, L. et al., "Green and selective polycondensation methods toward linear sorbitol-based polyesters: enzymatic VS. organic and metal-based catalysis," ChemSusChem, Issue 9, Jul. 13, 2016, pp. 2250-2260.

\* cited by examiner

RIGID FOAM COMPRISING A POLYESTER POLYOL

FIELD

The present invention relates to a rigid polyurethane foam comprising a polyester polyol which can be of bio-sourced origin.

BACKGROUND

Polyurethanes (PU) are versatile polymers and are used in various applications such as automobiles, furniture, construction, footwear, acoustic and thermal insulation with a global production of 18 Mt in 2016, placing the PU in the 6th rank among polymers based on the results of world annual production.

Today, the PU industry is highly dependent on petrochemical components such as polyether polyols obtained by alkoxylation reaction. Isocyanates are historically obtained from the chemistry of phosgene or diphosgene. According to various legislations, in particular under the Kyoto Protocol in Europe, it is now mandatory to reduce greenhouse gas emissions from production to the final use of a product. A very illustrative example of this is the increasing attention paid to building insulation, particularly the "bio-insulation" of individual and collective premises. One of the best materials for building insulation is rigid polyurethane foam (PUR), based on the polyaddition of polyols and high-functionality polyisocyanurates bearing 2 to 3 isocyanate groups to obtain closed cell materials. The thermal conductivity of PUR foams ranges from 20 mW/(mK) to 30 mW/(mK) versus 30 mW/(mK) and 40 mW/(mK) for expanded polystyrene (EPS) or 40 mW/(mK). 50 mW/(MK) for extruded polystyrene (XPS). PUR foams now rival rigid polyisocyanurate-polyurethane (PUIR) foams that perform better than conventional PUR foams. PUIR foams are based on the trimerization at high temperature of diisocyanates to a isocyanurate ring also known as triisocyanuric ring (Scheme 1) in the presence of a specific catalyst. The PUIR foam formulation is slightly different from the PUR foams. Excess isocyanate function is required to obtain trifunctional isocyanurate rings.

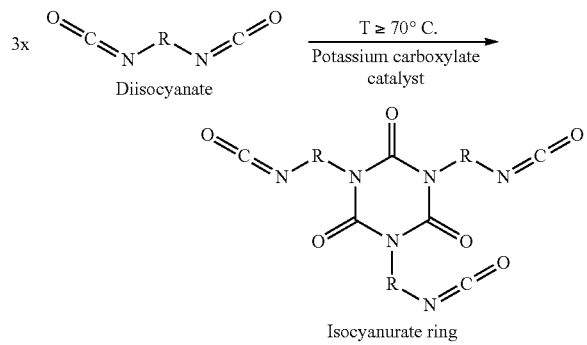

Scheme 1: Trimerization of Diisocyanate in the Presence of Potassium carboxylate catalyst Thus, a lower functionality polyol can be used. The PUIR foam network is based on a double chemistry. The polyol reacts with the isocyanate to form polyurethane. Then, the excess polyisocyanates trimerize in isocyanurate ring giving rise to the high density of crosslinking of the final foam. The high density of crosslinking PUIR foams is their main disadvantage because it induces friability to the material.

The friability of PUIR foams is largely compensated by their superior properties vis-à-vis the PUR foams, in particular by their higher thermal resistance. It has been established that the range of thermal stability of the urethane function depends on their chemical environment and evolves between 120° C. and 250° C. The thermal stability range of the isocyanurate function also depends on the surrounding chemical function, but is estimated between 365° C. and 500° C. The better thermal stability of the isocyanurate functions present in PUIR foams is at the origin of their better fire resistance compared to PUR foams. The thermal resistance of PUIR foams over PUR foams makes them really attractive in the building insulation sector. The building and construction sectors are facing new standards that are more and more drastic vis-à-vis thermal and fire resistance for the used materials. Despite these superior properties, little research has been done on the PUIR system depending on the substitution of the petroleum-based polyol with a sorbitol-based polyol derived from biomass or a formulation containing 100% renewable polyol.

Recently, only rapeseed oil, crude glycerol, castor oil, microalgae and tannin-based polyols have been used in PUR-PUIR foam.

The properties of PUIR foams are mainly related to their morphology and internal structure, which has a significant effect on thermal conductivity and mechanical properties. It is well established that the thermal properties of foam materials depend mainly on the closed cell content and the gas they contain (H. Fleurent and S. Thijs, J. Cell. Plast., 1995, 31, 580-599). It is also well accepted that the mechanical properties of expanding materials are closely dependent on their density. J. Mills (N. J. Mills, J. Cell. Plast., 201 1, 47, 173-197) investigated closed-cell polyethylene and polystyrene foams and showed that the air included in the cells contributed significantly to the compression strength of low-density foams. Nevertheless, the mechanical properties of PUIR foams are often not well studied. J. Andersons et al. (J. Andersons et al., Mater. Des., 2016, 92, 836-845). worked on partially biosourced, low-density and closed-cell polyisocyanurate foams.

They studied the anisotropy of the foam resistance to compression from the longitudinal and transverse direction to the rise of the foam. They showed that the ratio between the Young's moduli and the force the longitudinal direction and the transverse direction were respectively about 3 and 1, 4.

SUMMARY

The present invention aims to develop a new PUIR foam prepared from biosourced products and more particularly a bio-sourced polyester polyol likely to replace the current petroleum-based polyols used for foams in the market, in their traditional application. The object of the present invention is to provide a biosourced foam having mechanical and physical properties comparable to petroleum-based foams, for example in terms of cell size of thermal degradation, kinetics, foaming, hardness, compressibility, density or thermal conductivity.

DETAILED DESCRIPTION

The invention relates to rigid foam or a composition for obtaining a rigid foam comprising a polyester polyol or a polymer comprising a polyester polyol, said polyester polyol being obtained by a first polycondensation (a) of a C3 to C8 sugar alcohol Z and two identical or different C4 to C36 diacids Y and Y' and a second polycondensation (b) of the product obtained in (a) with two identical or different C2 to C12 X and X' diols.

The invention also relates to a rigid foam or a composition for obtaining a rigid foam comprising a polyester polyol or a polymer comprising a polyester polyol, said polyester polyol is of general formula Rx-Ry-Z-Ry'-Rx' in which Z is a sugar alcohol having C3 to C8, preferentially C4 to C7, typically C5, C6, Ry and Ry' are diesters of formula —OOC—$C_n$—COO— with n between 2 and 34, preferably between 3 and 22, typically between 4 and 10, Rx and Rx' are monoalcohols, which are identical or different having C2 to C12, preferably C3 to C8, typically C4.

Typically, by the term "foam" as used, for example, in the terms "polyurethane foam" or "polyisocyanurate foam" is meant a compound of of three-dimensional expanded type alveolar structure. Said foam may be rigid or flexible, with open or closed cells. The term "rigid foam" means a foam having a good compressive strength and whose internal structure is irreversibly damaged during compression deformation of between 5 and 50%. Generally, such foams have glass transition temperatures (Tg) greater than 100° C. often close to 200° C. Rigid foams are generally foams with a high closed cell content (generally greater than 90%).

Rigid polyurethane (PUR), or rigid polyisocyanurate (PUIR) refer to rigid foams of polyurethane or polyisocyanurate.

The term "closed cell foam" means a foam of which the alveolar structure comprises walls between each cell that form a set of attached and separate cells allowing for the imprisonment of an expansion gas. A foam is qualified as a closed cell foam when it has a maximum of 10% of open cells. Typically, closed cell foams are mostly rigid foams.

The term "open cell foams" means a foam whose alveolar structure is formed of a continuous cell matrix with an open wall between the cells which do not allow for the imprisonment of an expansion gas. Such a foam allows for the creation of percolation paths within the cell matrix thereof. Typically, open cell foams are mostly flexible foams.

The term "polyester polyol" refers to molecules that comprise hydroxyl groups (diols or sugar alcohols) bonded together by ester bonds. Thus, in the polyester polyol according to the invention, the molecules X, Y, Z, Y' and X' are bonded together by ester bonds. Typically, the diols X and X' and the sugar alcohol Z are bonded to the two diacids Y and Y' by ester bonds each formed between an acid function of Y or of Y' and a primary hydroxyl function of Z, X or X'. Advantageously, the polyester polyol is of neutral pH, typically, when it is obtained by two successive polycondensations followed by a step of neutralisation (for example with potash or with sodium hydroxide).

The polyester polyol according to the invention advantageously has the general chemical formula $C_aH_bO_c$ having $22 \leq a \leq 42$, $38 \leq b \leq 78$, $14 \leq c \leq 22$.

Typically, the polyester polyol according to the invention has a molecular weight of between 350 g/mol and 2000 g/mol, preferably between 420 g/mol and 1800 g/mol and more preferably between 450 and 1700 g/mol. According to the invention, the molar weight of the polyester polyol can be determined by various methods such as size exclusion chromatography.

Advantageously, the polyester polyol has a hydroxyl number of 300 to 900 mg KOH/g. The hydroxyl number (IOH) can be calculated with the following formula:

IOH=functionality of polyester polyol×56109.37/ Molar mass of polyester polyol.

The hydroxyl number corresponds to the number of mg of KOH necessary to deprotonate all the hydroxyl groups present in one gram of polyol. The hydroxyl number can be determined by reverse assay using potassium hydroxide, for example according to ASTM 4274-99 in which the colorimetric titration is replaced by a pH-metric titration.

The term "sugar alcohol" or "polyol" means a hydrogenated form of monosaccharide of which the carbonyl group (aldehyde or ketone) has been reduced to a primary or secondary hydroxyl. Typically, sugar alcohol is chosen from glycerol, sorbitol, erythritol, xylitol, araditol, ribitol, dulcitol, mannitol and volemitol.

The term "diacid" means a carbon chain comprising two acid groups. According to the invention, the polyester polyol comprises two molecules Y and Y' of diacid. These molecules can be identical or different in C4 to C36, preferably C4 to C24. Typically, the two molecules of diacid are independently chosen from butanedioic acid (Succinic acid), pentanedioic acid (Glutaric acid), hexanedioic acid (Adipic acid), heptanedioic acid (Pimelic acid), octanedioic acid (Suberic acid), nonanedioic acid (Azelaic acid), decanedioic acid (Sebacic acid), undecanedioic acid, dodecanedioic acid, tridecanedioic acid (Brassylic acid), tetradecanedioic acid, pentadecanedioic acid, hexadecanedioic acid, fatty acid dimers having up to 36 carbons (C36) or mixture thereof. Typically, Y and Y' are diacids in C5 to C16 or C6 to C12. Advantageously, the preferred molecules of diacid are independently chosen from adipic acid and succinic acid.

The term "diol" means a carbon chain comprising two alcohol functions. According to the invention, the polyester polyol comprises two molecules X and X' of diols which are identical or different. Typically, the molecules of diol are independently chosen from 1,2 ethanediol, 1,3 propanediol, 1,4-butanediol, 1,6 hexanediol, 1,8 octanediol, 1,10 decanediol, 1,12 dodecanediol and mixtures thereof.

Advantageously, the polyester polyol according to the invention is chosen from bis(1,2 ethanediol)-sorbitol diadipate, bis(1,3 propanediol)-sorbitol diadipate, bis(1,4-butanediol)-sorbitol diadipate, bis(1,4-butanediol)-sorbitol diadipate modified with glycerol, bis(1,6 hexanediol)-sorbitol diadipate, bis(1,8 octanediol)-sorbitol diadipate, bis(1,10 decanediol)-sorbitol diadipate, bis(1,12 dodecanediol)-sorbitol diadipate, bis(1,4 butanediol)-sorbitol disuccinate and sorbitol-diadipate-sorbitol. Preferably, said polyester polyol is chosen from bis(1,8 octanediol)-sorbitol diadipate, bis(1,10 decanediol)-sorbitol diadipate and bis(1,4-butanediol)-sorbitol diadipate.

The invention also relates to a flexible or semi-flexible foam or a composition for obtaining a flexible or semi-flexible foam comprising a polyester polyol obtained by a process comprising the following steps:

a) a step of polycondensation at a temperature between 110 and 200° C., preferably, 120 to 180° C., more preferably, 130 and 170° C., typically 150° C., advantageously for 5 to 10 hours:
   i. of a sugar alcohol Z in C3 to C8, preferably in C4 to C7, advantageously in C5-C6, typically chosen from glycerol, sorbitol, erythritol, xylitol, araditol, ribitol, dulcitol, mannitol and volemitol,
   ii. of two diacids Y and Y' which are identical or different in C4 to C36, preferably in C5 to C24, iii. of two diols X and X' which are identical or different in C2 to C12, preferably in C3 to C8, typically in C4 advantageously, independently chosen from 1,2 ethanediol, 1,3 propanediol, 1,4-butanediol, 1,6 hexanediol, 1,8 octanediol, 1,10 decanediol, 1,12 dodecanediol, 1,4 butanediol and mixtures thereof, b) optionally, a step of neutralisation of the free acid functions in such a way as to bring back the polyester polyol to a neutral pH (pH=7), for example, via a base typically, a strong base such as potash or with a weak base such as sodium carbonate, sodium bicarbonate, potassium carbonate or a mono- bi- or trialcohol in C4 to C8, such as hexanol; preferably the step of neutralisation is carried out by adding potassium carbonate or potassium hydroxide.

Advantageously, during the polycondensation step, the diols X and X' and the sugar alcohol Z are at a molar ratio (X+X')/Z of between 1 and 3, preferably between 1.5 and 2.5, more preferably between 1.8 and 2.2.

Typically, during the polycondensation step, the diacids Y and Y' and the sugar alcohol are at a molar ratio (Y+Y')/Z of between 1 and 3, preferably between 1.5 and 2.5, even more preferably between 1.8 and 2.2.

According to one embodiment, during the polycondensation step, the diols X and X' and the diacids Y and Y' are at a molar ratio (X+X')/(Y+Y') of between 0.5 and 2, preferably between 0.7 and 1.5, even more preferably between 0.8 and 1.2.

Advantageously, the polycondensation step comprises a first polycondensation (a) of the sugar alcohol Z and diacids Y and Y' and a second polycondensation (b) of the product obtained in (a) with the diols X and X'. This polycondensation in two stages makes it possible to obtain the polyester polyol with this symmetric structure. Typically, the diacids Y and Y' are identical and/or the diols X and X' are identical.

According to one embodiment, the sugar alcohol Z is mixed with the diacid molecule(s) Y and Y' and then incubated for more than one hour, more preferably between 2 and 5 hours, even more preferentially between 2.5 and 4 hours, typically for 3 hours. The diol molecule(s) X and X' are added in a second step to the mixture and then incubated for more than 4 hours, preferably between 5 and 10 hours, typically between 5.5 and 7 hours. Preferably, the polycondensation step is carried out under vacuum.

Advantageously, during the polycondensation step, the diacid molecules Y and Y' react with the primary alcohols of sugar alcohol molecules Z and diols X and X'. The water molecules resulting from the reaction are recovered in view of being eliminated.

The invention further relates to a rigid foam or a composition for obtaining a rigid foam, comprising a polymer comprising the polyester polyol according to the invention, typically, said polymer is a polyurethane and/or a polyisocyanurate.

Advantageously, the polymer according to the invention has a molar mass greater than $1.7 \times 10^6$ g/mol. Typically, the polymer is a crosslinked polymer.

By "polyurethane" is meant a polymer comprising urethane functions, that is in other words, a urethane polymer. These polymers result essentially from the reaction of polyols, in particular the polyester polyols of the invention with polyisocyanates. These polymers are generally obtained from formulations having an index from 100 to 150, preferably from 105 to 130 corresponding to a NCO/OH ratio of between 1 and 1.5, preferably between 1.05 and 1.3.

By "polyisocyanurate" is meant the polymer resulting from the reaction of polyols, in particular the polyester polyol of the invention and polyisocyanates, which contain, in addition to urethane linkages, other types of functional groups, in particular rings. triisocyanuric compounds formed by the trimerization of polyisocyanates. These polymers, normally also called modified polyurethanes or polyisocyanurates-polyurethanes, are generally obtained from formulations having an index of 150 to 700, preferably between 200 and 500, even more preferably between 250-400, or an NCO/OH ratio of between 1.5 and 7.0 preferably between 2.0 and 5.0, preferably between 2.5 and 4.0.

According to the invention, said polymer is a mixture of polyurethane and polyisocyanurate. Such a mixture is observed for example when said polymer comprises urethane functions polyisocyanates trimerized to triisocyanuric rings. Typically, said polymer is a mixture of polyurethane and polyisocyanurate and has an index greater than 100 or less than or equal to 400, corresponding to an NCO/OH ratio greater than 1 or less than or equal to 4.

The term NCO/OH ratio means, in terms of this invention, the ratio between the number of NCO functions of the polyisocyanate and the number of OH functions of the polyol polyester, co-polyols and of any other component present in the formulation comprising OH groups (water, solvents). The NCO/OH ratio is calculated with the following formula:

$$\text{NCO/OH ratio} = M_{exp}Pi \times ME\ Pi / M_{exp}SAI \times ME\ SAI$$

where:

$M_{exp}Pi$ is the mass of the polyisocyanate;

$M_{exp}SAI$ is the mass of the sugar alcohol;

ME SAI is the equivalent mass of the sugar alcohol and corresponds to the ratio between the molar mass of the sugar alcohol and the functionality of the sugar alcohol;

MEPi is the equivalent mass of the polyisocyanate and corresponds to the ratio between the molar mass of the polyisocyanate and the functionality of the polyisocyanate.

In the present invention, the term "urea bond" means a disubstituted urea linkage or the product of the reaction between a primary amine and an isocyanate function of a polyisocyanate.

Primary amines can be introduced into the composition or are the product of the reaction between a water molecule and an isocyanate function of a polyisocyanate.

Typically, the rigid foam or the composition for obtaining such rigid foam comprising the polyester polyol according to the invention or the polymer according to the invention, namely the pre-polymer, further comprises, at least one reaction catalyst, at least one swelling agent, a stabilizer, at least one polyisocyanate having a functionality of at least 2, optionally one co-polyol and additives.

By "co-polyol" is meant a compound carrying two or more hydroxyl functions (diol type) (polyol) added to the composition comprising the polyester polyol in order to adjust the properties thereof such as the functionality or the viscosity, to create crosslinking nodes or chain extension.

The foam according to the invention comprises at least one co-polyol of C2 to C8, preferably C2 to C7, advantageously C2 to C6. The at least one copolyol may advantageously be chosen from ethylene glycol, glycerol, 1,4-butanediol, butane-1,3-diol, 1,3-propanediol and propane-1,2-diol. pentanediol, 1,6-hexanediol, 1,2-propylene glycol, 3-oxapentane-1,5-diol, 2-[2-(2-hydroxyethoxy) ethoxy] ethanol, benzene-1,2,4-triol, benzene 1,2,3-triol, benzene 1,3,5-triol sorbitol, erythritol, xylitol, araditol, ribitol, dulcitol, mannitol and volemitol. Preferably, the at least one co-polyol is selected from glycerol, ethylene glycol, 1,4- butanediol, 1,3-propanediol, 1,5-pentanediol, 1,2-propylene glycol and 3-oxapentane 1,5-diol, and sorbitol. The preferred at least one co-polyol is selected from glycerol, ethylene glycol, 1,4-butanediol and sorbitol.

Typically, the co-polyol(s) is/are added in a polyol polyester/co-polyol (s) ratio of 70/30 to 99/1, preferably 75/25 to 95/5, even more preferably between 80/20 a, d 92/8, typically between 82/8 and 90/10, for example 85/15.

According to the invention, the composition comprises two co-polyols, typically a co-polyol C2 and a co-polyol C3 or a co-polyol C2 and a co-polyol C4 or a co-polyol C2 and a co-polyol C5 or a co-polyol C2 and a co-polyol C6 or a co-polyol C3 and a co-polyol C4 or a co-polyol C3 and a co-polyol C5 or a co-polyol C3 and a co-polyol C6 or a C5 co-polyol and a co-polyol C6 or two co-polyols C3 or two co-polyols C4 or two co-polyols C5 or two co-polyols C6.

Advantageously, the composition comprises at least one C2 co-polyol, typically two co-polyols, for example a C2 co-polyol and one C3 or C4 or C5 or C6 co-polyol, typically ethylene glycol and glycerol, ethylene glycol and erythritol, ethylene glycol and xylitol, ethylene glycol and araditol, ethylene glycol and ribitol, ethylene glycol and dulcitol, ethylene glycol and mannitol, ethylene glycol and 1,4-butanediol, ethylene glycol and 1,3-propanediol, 1,3-propanediol and 1,4-butanediol, or ethylene glycol and volemitol. According to the invention, the preferred mixture of co-polyols is glycerol and ethylene glycol. For example, the composition comprises two co-polyols, typically erythritol and sorbitol, xylitol and sorbitol, araditol and sorbitol, ribitol and sorbitol, dulcitol and sorbitol, mannitol and sorbitol or volemitol and sorbitol.

Advantageously, the composition comprises two co-polyols typically in a ratio C2/C6 or C2/C5 or C2/C6 or C2/C3 or C3/C6 or C3/C5 or C5/C6 ranging from 95/05 to 50/50, preferably from 90/10 to 55/45, preferentially from 87/13 to 60/40, more preferably from 85/15 to 62/38, even more preferably from 80/20 to 65/35.

The term "polyisocyanate" means any chemical compound comprising at least two separate isocyanate chemical functions (NCO), in other words, that have "a functionality at least equal to 2". When the polyisocyanate has a functionality of 2, this is referred to as di-isocyanate. The term functionality means, in terms of this invention, the total number of reactive isocyanate functions per molecule of isocyanate. The functionality of a product is evaluated via the titration of the NCO function by a method of return dosage of the excess dibutylamine by the chloridric acid. Typically, said polyisocyanate has a functionality between 2 and 5, preferably between 2.5 and 3.5 even more preferably between 2.7 and 3.3. Advantageously, said polyisocyanate is chosen from aromatic, aliphatic, cycloaliphatic polyisocyanates and mixtures thereof. Mention can be made for example of 2,4-toluene diisocyanate, 2,6-toluene diisocyanate, mixtures of 2,4- and 2,6-toluene diisocyanate, m-phenylene diisocyanate, p-phenylene diisocyanate, cis/trans of cyclohexane diisocyanate hexamethylene diisocyanate, m- and p-tetramethylxylylene-diisocyanate, m-xylylene, p-xylylene diisocyanate, naphthalene-m, m-diisocyanate, 1,3,5-hexamethyl mesitylene triisocyanate, 1-methoxyphenyl-2,4-diisocyanate, 4,4'-diphenyl-methane diisocyanate, 4,4'-diisocyanabiphenylene 3,3'-dimethoxy-4,4'-diphenyl diisocyanate, 3,3'-dimethyl-4,4'-diphenyl diisocyanate, 4,4'', 4''-triphenylmethane triisocyanate, toluene-2,4,6m-triisooyanate, 4,4'-dimethyl diphenyl methane-2,2',5,5'-tetraisocyanate, and aliphatic isocyanates, such as hydrogenated 4,4'-diphenylmethane diisocyanate, hydrogenated toluene diisocyanate (TDI) and hydrogenated meta- and paraxylene diisocyanate of tetramethylxylylene diisooyanate (TMXDI® isooyanate, product of American Cyanamid co, Wayne, N.J., USA.), 3:1 meta-tetramethylxylylene diisocyanate/trimethylolpropane (Cythane 3160® isocyanate, from the company American Cyanamid Co.), plurifunctional molecules such as poly-diisocyanate of diphenylmethylene (pMDI) and the analogues thereof.

Typically, the polyisocyanate is chosen from toluene diisocyanate (TDI), 4,4'-diphenylmethane diisocyanate (or 4,4'-diisocyanate of diphenylmethylene or 4,4'-MDI), polymethylene polyphenylene polyisocyanate (polymeric MDI, pMDI) and mixtures thereof.

The term "reaction catalyst" means a compound that introduced in a small quantity accelerates the kinetics of the formation of the urethane bond (—NH—CO—O—) by reaction between the polyester polyol of the invention and a polyisocyanate or activates the reaction between a polyisocyanate and water or activate the trimerisation of the isocyanates. Typically the reaction catalysts are chosen from tertiary amines (such as dimethylcyclohexane), derivatives of tin (such as tin dibutyldilaurate), ammonium salts (such as methanaminium N,N,N-trimethyl of 2,2-dimethylpropanoate), carboxylates of alkali metals (such as potassium 2-ethylhexanoate or potassium octoate) amine ethers (such as bis(2-dimethylaminoethyle) ether), and triazines (such as 1,3,5-Tris(3-(dimethylamino)propyl))hexahydro-1,3,5-triazine).

Advantageously, a composition intended for obtaining a foam compriseing said polyester polyol according to the invention or said polymer, namely pre-polymer, according to the invention, at least one reaction catalyst, at least one polyisocyanate having a functionality at least equal to 2, at least one swelling agent, a stabilizer and optionally a flame retardant, a co-polyol.

Advantageously, when the composition is a foam or a composition making it possible to obtain a foam, the preferred polyester polyol is a neutral pH polyester polyol and/or comprises sorbitol as sugar-alcohol Z. Typically, the polyester polyol preferred is bis (1,2-ethanediol)-sorbitol-diadipate, bis (1,6-hexanediol) sorbitol-diadipate or bis (1,4-butanediol)-sorbitol-diadipate, more preferably, bis (1,4-butanediol)-sorbitol. diadipate, or bis (1,6 hexanediol)-sorbitol-diadipate.

According to the invention, a foam typically comprises, after polymerization, a polymer according to the invention, in particular a crosslinked polymer, at least one reaction catalyst, at least one swelling agent, at least one stabilizer, and optionally at least one co-polyol.

By "swelling agent" is meant a compound inducing by a chemical and/or physical action an expansion of a composition during a foaming step. Typically, the chemical swelling agent is chosen from water, formic acid, phthalic anhydride and acetic acid. The physical swelling agent is chosen from pentane and pentane isomers, hydrocarbons and hydrofluorocarbons, hydrochlorofluoroolefins, hydrofluoroolefins (HFOs), ethers and their mixtures thereof. Methylal may be mentioned as an example of an ether-type swelling agent. According to the invention, a preferred chemical and physical swelling agent mixture is, for example, a water/pentane isomer mixture or formic acid/pentane isomer or water/hydrofluoroolefins or pentane isomer/methylal/water or else water/methylal.

By "stabilizer" is meant, an agent allowing the formation of an emulsion between the polyol and the swelling agent, the formation nuclei sites of expansion of the swelling agent, as well as the physical stability of the polymer matrix during progress of the reactions. Typically, the stabilizers are chosen from any of the silicone glycol copolymers (for example Dabco DC198 or DC193 sold by Air Products), non-hydrolyzable silicone glycol copolymer (for example DC5000 from Air Products), polyalkylene siloxane copolymer (for example Niax L 6164 from Momentive), polyoxyalkylene methylsiloxane copolymer (for example Niax L-5348 from Momentive), polyetherpolysiloxane copolymer (for example Tegostab B8870 or Tegostab B1048 from Evonik), polydimethylsiloxane polyether copolymer (for example Tegostab B8526 from Evonik), polyethersiloxane (for example Tegostab B8951 from Evonik), a modified polyether-polysiloxane copolymer (for example Tegostab B8871 from Evonik), a block polyoxyalkylene polysiloxane copolymer (for example Tegostab BF 2370 from Evonik), derivatives thereof or mixtures thereof.

By "additives" is meant agents such as antioxidants (neutralisation agents of chain ends at the origin of the depolymerisation or co-monomer chains capable of stopping the propagation of depolymerisation), demoulding agents (talc, paraffin solution, silicone), anti-hydrolysis agents, biocides, anti-UV agents (titanium oxide, triazines, benzotriazoles) and/or flame retardants (antimony, phosphorus, boron, nitrogen compounds).

The term "flame retardant" means a compound that has the property of reducing or preventing the combustion or the heating of the materials that it impregnates or covers, referred to as flame or fire retardant. Mention can be made for example to graphite, silicates, boron, halogenated or phosphorous derivatives such as Tris (1-chloro-2-propyl) phosphate (TCPP), triethyl phosphate (TEP), triaryl phosphate esters, ammonium polyphosphate, red phosphorous, trishalogenaryl, and mixtures thereof.

An example of a composition according to the invention for obtaining a closed-cell rigid polyurethane foam is typically formulated with an index of between 101 and 200, preferably between 102 and 170, even more preferably between 105 and 150, for example 115, or an NCO/OH ratio of between 1, 01 and 2, preferably between 1.02 and 1.7, even more preferably between 1.05 and 1.5, for example 1.2.

Typically, such a composition comprises
  at least to 100 parts, preferably from 40 to 100 parts, even more preferably between 80 and 100 parts of a polyester polyol according to the invention,
  0 to 70 parts, preferably from 1 to 50 parts even more preferably between 2 and 30 parts of at least one co-polyol,
  150 to 500 parts, preferably 160 to 425 parts even more preferably between 180 and 375 parts of at least one polyisocyanate,
  0.5 to 5 parts of at least one catalyst typically of an amine catalyst such as dimethylcyclohexyleamine,
  0.5 to 15 parts of at least one swelling agent typically, 0.5 to 12 parts, preferably 0.6 to 10 parts, even more preferably 0.7 to 9 parts of a chemical swelling agent such as water and/or 0 to 60 parts, preferably 0.5 to 30 parts, even more preferably 1 to 25 parts of a physical swelling agent such as isopentane derivatives,
  0 to 5 parts of a stabilizer such as a polyether-polysiloxane copolymer, and
  0 to 20 parts of a flame retardant.

A closed cell rigid polyurethane foam comprises for example 100 parts of a polyester polyol, 270 parts of a polyisocyanate, 2 parts of an amine catalyst such as dimethylcyclohexyleamine, 6 parts of a swelling agent such as water, 2.5 parts of a stabilizer such as a polyether-polysiloxane copolymer and 10 parts of a flame retardant.

An example of a composition for obtaining a rigid closed cell polyisocyanurate foam is typically formulated with a minimum index of 200 or an NCO/OH ratio greater than 2.0, preferably an index of between 250 and 450, more preferably between 300 and 400, ie an NCO/OH ratio preferably of between 2.5 and 4.5, even more preferably of between 3.0 and 4.0.

A composition for obtaining a rigid closed cell polyisocyanurate foam comprises
  60 to 100 parts, preferably 70 to 100 parts even more preferably between 80 and 100 parts of the polyester polyol according to the invention,
  0 to 50 parts, preferably from 1 to 40 parts even more preferably between 5 and 20 parts of a co-polyol,
  100 to 700 parts, preferably from 120 to 650 parts, even more preferably between 150 and 575 parts of at least one polyisocyanate,
  0.1 to 13 parts, preferably from 0.5 to 12 parts, even more preferably between 1 and 11 parts of at least one catalyst, preferably two catalysts, typically an amine catalyst and a potassium carboxylate (for example in a catalyst ratio amine/potassium carboxylate 0.2 to 2),
  0 to 80 parts, preferably 5 to 70 parts even more preferably between 10 and 60 parts of at least one swelling agent such as an isomer of pentane,
  0 to 8 parts, preferably from 1 to 7 parts even more preferably between 1, 5 and 6 parts of a stabilizer
  0 to 30 parts, preferably 5 to 25 parts even more preferably between 10 and 20 parts of a flame retardant.

Typically, a composition for obtaining a closed cell polyisocyanurate rigid foam comprises, for example, 85 parts of the polyester polyol according to the invention; 15 parts of a co-polyol such as ethylene glycol; 550 parts of a polyisocyanate such as diphenylmethylene polyisocyanate; 1.6 parts of an amine catalyst such as bis (2-dimethylaminoethyl) ether; 7 parts of a potassium carboxylate such as, for example, potassium 2-ethylhexanoate; 0.8 parts of a triazine such as 1,3,5-tri (3-[dimethylamino] propyl) hexahydro-s-triazine; 45 parts of a swelling agent such as an isomer of pentane; 2.5 parts of a stabilizer and 15 parts of a flame retardant The invention also relates to a panel or a block of rigid foam comprising the rigid foam of the invention, typically for thermal or acoustic insulation, namely thermal or acoustic insulation of buildings or cryogenic insulation of refrigerators, gass-carrier vessel tanks, or for empty space filling or buoyancy help such as in buoyancy aids (belts or vests . . . ) or water sports, for the damping of shocks and vibrations (for example, shoes, carpets or mattresses, foams for packaging or padding hard structures in order to improve the comfort, typically roof lining, seating (seats, chairs . . . ), soles, areas for gripping for example the wheels of cars, . . . ), for filtration.

The term "panel" having approximately a rectangular parallelepiped shape having relatively smooth surfaces and the following dimensions from 0.3 to 50 $m^2$ of surface for a thickness of 10 to 1000 mm, preferably from 0.5 to 20 $m^2$ of surface for a thickness of 15 to 500 mm; even more preferably, from 0.8 to 15 $m^2$ of surface for a thickness 17 to 400 mm typically, from 1 to 7 $m^2$ of surface for a thickness of 20 to 250 mm Examples of dimensions are typically, a surface of 600×600 mm or 1200×600 mm for a thickness of 20 to 250 mm.

By block is meant a structure of any geometrical shape, cubic, parallelepiped, star-shaped or cylindrical, with or without recess(es), of a volume of between 1 $cm^3$ and 100 m³, preferably 10 cm³ to 70 m³, even more preferentially 100 cm³ to 50 m³ typically 0.5 to 35 m³, typically 1 to 30 m³.

The invention also relates to a method for obtaining a panel or a block of rigid block according to the invention.

The invention relates to a method for thermal, sound or cryogenic insulation, namely for buildings, fluid transport pipes or a method of filling (cracks or free space), sealing (structures, cracks, etc.)), waterproofing or improving the floatation (typically buoyancy aids or water sports) by depositing or introducing blocks or panels according to the invention or by the projection of a rigid foam or a composition for obtaining a rigid foam according to the invention.

The invention also relates to a process for obtaining a rigid foam, typically polyurethane or polyisocyanurate comprising:
- a step of obtaining a polyester polyol according to the invention or a polymer according to the invention, in particular a prepolymer according to the invention,
- a step of adding at least one polyisocyanate, at least one swelling agent, a stabilizer and at least one reaction catalyst, and
- a polymerization step.

Although having distinct meanings, the terms "comprising", "containing", "comprising" and "consisting of" have been used interchangeably in the description of the invention, and may be replaced by other. The invention will be better understood on reading the following figures and examples given solely by way of example.

Although having distinct meanings, the terms "comprising", "containing", "comprising" and "consisting of" have been used interchangeably in the description of the invention, and may be replaced by other.

The invention will be better understood on reading the following figures and examples given solely by way of example.

EXAMPLES

Figures 1A, 1B, 1C:
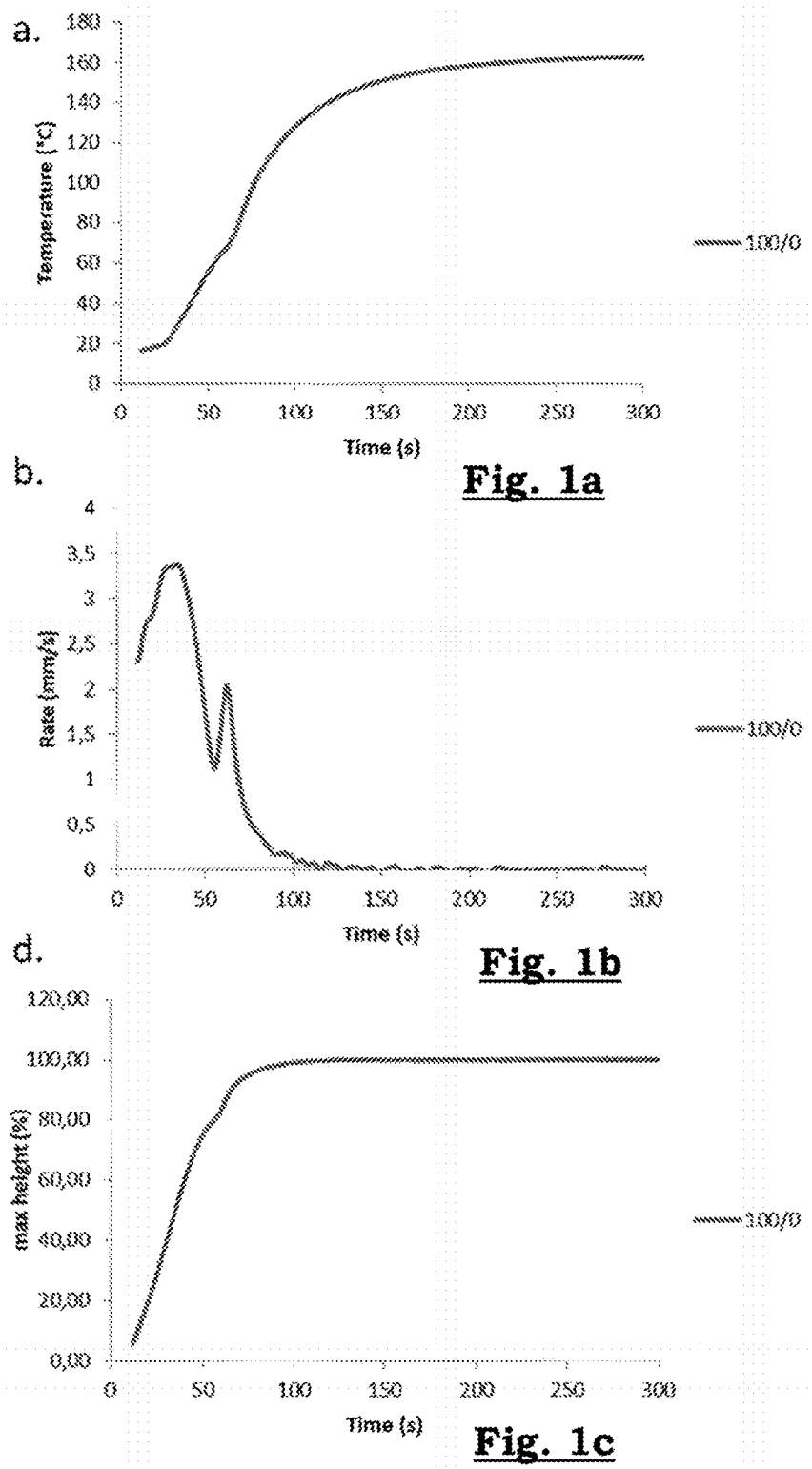
FIG. 1a: Petroleum-sourced PUIR Foaming Profile: temperature.
FIG. 1b: Petroleum-sourced PUIR Foaming Profile: expansion speed.
FIG. 1c: Petroleum-sourced PUIR Foaming Profile: maximum standardized height of the foam.

1. Material and Method
   a. Reagents

The petroleum-based polyester polyol is an aromatic polyester based on modified phthalic anhydride of STEPANP (STEPANPOL® PS-2412), called petroleum-based polyol. The biosourced polyester polyol (BASAB) was obtained from sorbitol according to an esterification process described in our patent application FR 16/01253. The properties of the petroleum-based and biosourced polyols are summarized in Table 1. D-sorbitol marketed by TEREOS SYRAL (sorbitol greater than 98%, water less than 0.5%, reducing sugars below 0.1%), 1,4 butanediol (99%) is marketed by SIGMA ALDRICH, adipic acid (99%) marketed by ACROS ORGANICS. The polyisocyanate is polymeric 4,4'-methylenebis (phenyl isocyanurate) (MDI) and N,N-dimethylcyclohexylamine (DMCHA catalyst) is from BORSODCHEM (Ongronat 2500). Various crude catalysts such as 1,3,5-tris (3-[dimethylamino] propyl)-hexahydro-triazine provided by EVONIK (Tegoamin C41), bis (2-dimethylaminoethyl) ether from BASF (Lupragen N205), 15% in weight. Potassium octoate (Ko) solution and 40% by weight. Potassium carboxylate in ethylene glycol (Pc) from EVONIK was used. The flame retardant used is SHEKOY tris (1-chloro-2-propyl) phosphate (TCPP), the surfactant is polydimethylsiloxane (B84501) from EVONIK and ethylene glycol (EG) was obtained from ALFA AESAR (purity 99%). INVENTEC isopentane was used as a swelling agent. All of these chemicals were used as received without further purification.

TABLE 1

Principal properties of the petroleum based polyether polyol and BASAB.

| | Hydroxyl index (mg KOH/g) | Acidity index (mg KOH/g) | Viscosity at 25° C. (mPa · s) | Primary Hydroxyls | Secondary Hydroxyls | Surface Tension (mN/m) |
|---|---|---|---|---|---|---|
| petroleum-based polyether polyol | 230-250 | 1.9-2.5 | 4000 | 2 | 0 | 33.6 ± 0.9 |
| BASAB | 490-510 | less than 3 | 14000 | 2 | 4 | 40 ± 0.8 | b. General Method of Obtaining BASAB

The reaction is carried out in a sealed stainless steel reactor equipped with a U-shaped stirring flask, a Dean Stark having an outlet at the top of the condenser to be able to link a vacuum pump and a low output to recover the condensates, an inlet and an outlet of inert gas. In the reactor, sorbitol and adipic acid are introduced in powder form in a 1/2 molar ratio (sorbitol/adipic acid). The reactor is placed in an inert atmosphere and then heated. When the temperature reaches 100° C., stirring is progressively increased to 170 rpm. When the temperature reaches 150° C., the reaction is started and continued for 3 hours. After 3 hours, 1,4 butanediol (called diol hereinafter) is introduced into the reactor in a molar ratio (1,4 butanediol/sorbitol) 2.2/1. The temperature of the reaction medium returns to 150° C. (stirring still maintained at 170 rpm, inert atmosphere). 2 h30 after the return to 150° C. a passage under partial vacuum is carried out under partial vacuum for a period of one minute then atmospheric pressure is brought back under an inert atmosphere. 4 h30 after the addition of diols, a new flush of partial vacuum is carried out for 2 minutes then the atmospheric pressure is brought under an inert atmosphere. 6 h15 minutes after the introduction of the dioi (ie a total reaction time of 9 h 15 min at 150° C.), the reactor is stopped and the reaction product is recovered hot so as to have a minimum loss during the transfer of material from the reactor to the conditioning of the product.

c. General Method of Preparing Foams PUIR

The isocyanate/hydroxyl molar ratio (NCO/OH) was maintained at 3.2 in all PUIR formulations, to determine the amount of isocyanate, all the reactive hydroxyl groups are taken into account, namely polyols, water and solvents coming from the batch of the chosen catalysts. On the basis of the two-component foaming process, a first mixture was prepared containing polyols, catalysts, surfactants (poiydimethylsiloxane, B84501), flame retardants (TCPP), swelling agent (isopentane) and water. In each preparation, the number of parts (p) of the water, the TCPP, the surfactants are constant at 0.9p, 15p, 2.5p, respectively, and the total amount of polyol never exceeds 100p. The amount of swelling agent was kept constant at 24% to obtain foams of comparable densities. The mixture was mechanically stirred until a fine white emulsion was obtained with complete incorporation of the swelling agent. The mixture and the temperature of the polyisocyanates were checked and adjusted to 20° C. Then, the appropriate amount of polyisocyanate allowing an NCO/OH ratio of 3.2 was quickly added with a syringe to the emulsion. The entire reaction mixture was stirred vigorously for 5 seconds, and the foam was allowed to expand freely in a 250 mL disposable beaker at room temperature (controlled at 20° C.) or in a FOAMAT device. The characteristic constants of foaming kinetics were noted, namely cream time, string time and tack-free time. Prior to analysis, the foam samples were stored at room temperature for three days to achieve complete dimensional stability (no shrinkage).

A formulation containing only a petroleum-based polyester polyol was considered as a reference formulation (Table 1). This formulation is transposed to formulations containing 65% and 100% (equivalent to 65p and 100p, respectively) of BASAB indicated as 35/65 and 0/100 (PS2412/BASAB), respectively. The formulation was then optimized in formulations containing 85% (equivalent to 85 parts) of BASAB. Formulations containing BASAB are shown in Table 3.

TABLE 2

PUIR foam formulation indicated in parts

|  |  | N° Parts |
|---|---|---|
| Polyols | Petroleum-based | 100 |
| Catalyst | C41 | 0.3 |
|  | N205 | 0.12 |
|  | Ko | 3 |
| other | Water | 1 |
|  | Surfactant | 2.5 |
|  | Flame retardant | 15 | d. Characterizations

Thermogravimetric (TGA) analyzes were performed using a TA Hi-Res TGA Q5000 instrument in reconstituted air (flow rate 25 mL/min). 1-3 mg samples were heated from room temperature to 700° C. (10° C./min). The main characteristic degradation temperatures are those at maximum of the weight loss derived curve (DTG) ($T_{deg,\ max}$) and characteristic temperatures corresponding to 50% ($T_{deg50\%}$) and 100% ($T_{deg100\%}$) weight loss have been reported. Infrared spectroscopy was performed with a Fourier Nicolet 380 transformed infrared spectrometer used in reflection mode equipped with an ATR diamond module (FTIR-ATR). An atmospheric background was collected before each sample analysis (64 scans, resolution 4 cm$^{-1}$). All spectra were normalized on a C—H stretch peak at 2950 cm$^{-1}$.

Foam temperature, height and expansion rates, density and pressure were recorded using a FOAMAT FPM 150 (Messtechnik GmbH) equipped with cylindrical vessels, 180 mm high and 150 mm in diameter, an ultrasonic probe LR 2-40 PFT recording foam heights, a NiCr/Thermocouple Ni type K and a pressure sensor FPM 150. The data was recorded and analyzed with specific software.

Closed cell content is determined using a Quantachrome Instruments Ultrapyc 1200e based on the technique of gas expansion (Boyle's Law). Cubic samples of foams (approximately 2.5 cm×2.5 cm×2.5 cm) are cut for the first measurement, then the sample is cut once more into eight pieces and the measurement repeated. The second step is to correct the contents of the closed cells based on cells that have been damaged due to the cut of the sample. Measurements were made according to EN ISO4590 and ASTM 6226.

Foam cell morphology was observed with Jeol JSM-IT100 electronic emission scanning electron microscope (SEM). The cubic foam samples were cut with a microtome blade and analyzed in two characteristic orientations: longitudinal and transverse to the direction of the foam surges. Using the ImageJ (Open Source Processing Program) software, the average size of the cell was measured as the aspect ratio of the cell defined by equation 1.

$$R = \frac{1}{n}\sum_{i=1}^{n} \frac{D_F^{max}}{D_F^{min}}$$

Where $D_{Fmax}$ and $D_{Fmin}$ have maximum and minimum Feret diameters, n is the number of cells measured for a given sample.

II. Results and Discussion a. Kinetics of PUIR Reference Foam

The petroleum-based (100/0) PUIR foam exhibits rapid foaming with characteristic times shown in Table 3. In order to evaluate the foaming kinetics of these different formulations, the characteristic times of cream, string time and tack-free time were measured.

The cream time represents the initiation of the polyaddition reaction between the isocyanate functions provided by the polyisocyanates and the water or alcohol groups provided by all the polyols, co-polyols or additives present in the formulation. The cream time is characterized by a color change of the reaction medium before the expansion of the foam.

The String time represents the beginning of the formation of the polyurethane and/or polyisocyanurate polymer network. It is characterized by the formation of sticky string when physical contact is made with the expanding foam.

The tack-free time represents the end of the polymerization of the polyurethane and/or polyisocyanurate network at the surface of the foam. It is characterized by a foam that is no longer sticky to the touch.

Figure 3:
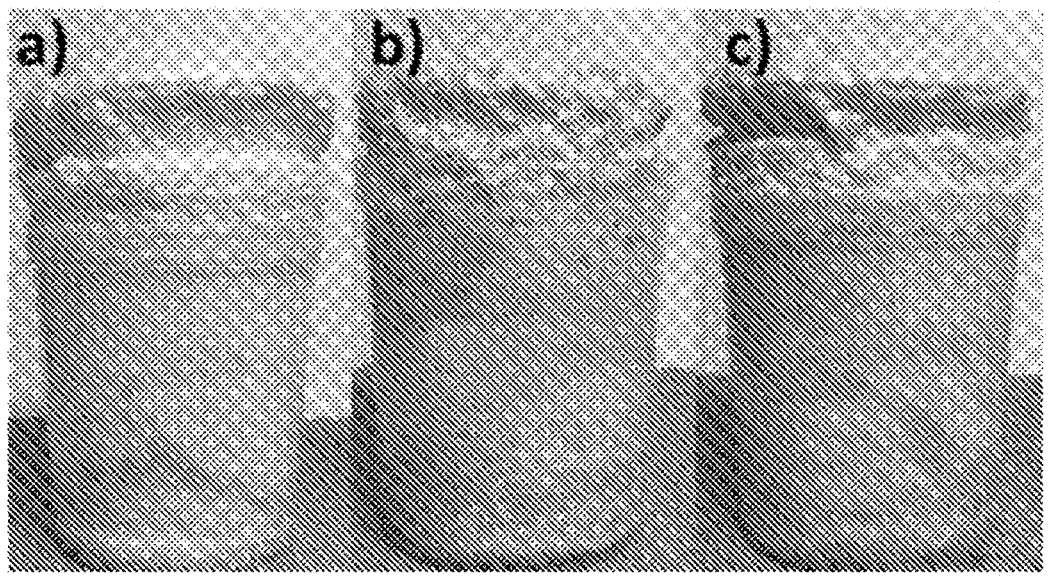
FIG. 3: Appearance of PUIR foams: a) 100/0, b) B1-K0, c) B2-PC.

The characteristic times recorded for 100/0 are 10 s, 60 s and 148 s for the cream time, lead time and tack time, respectively. The macroscopic appearance of such a PUIR foam is characteristic (FIG. 3a) and has a typical neck induced by the second growth of the foam during the trimerization of isocyanates. This second growth is really visible on the Foamat measurements presented in FIG. 1, b.

The expansion rate of the foam begins to decrease after 30 s of reaction and increases again after 60 s of reaction. The foam temperature curve (FIG. 1a) also shows a point of inflection at 50 s and increases up to 150° C., which corresponds to the trimerization of the isocyanates. The same phenomenon is visible in FIG. 1c, representing the maximum height of the foam. After 50 s, a variation of the slope is observed and the maximum height increases rapidly from 80 to 100% with the trimerization of the isocyanates.

b. Kinetics of PUIR Foams Containing BASAB

Two formulations similar to reference (100/0) containing only PS 2412 were made with the following polyester polyol ratios: 35/65 and 0/100 (parts/parts) of PS 2412/BASAB (Table 3). Analysis of the cream time of the formulations 35/65 and 0/100 shows that the beginning of the polyaddition reaction between the polyols and the polyisocyanates is shifted from the reference by 9 and 14 s, respectively. The string time of the 0/100 foam is not measurable because it is certainly confused with the tack-free time superiot to 300 s while the reference has a tack-free time 148 s. The comparison of these two tack-free times clearly shows that the catalyst mix traditionally used for the formulation containing 100% petroleum-based polyol is not as suitable for the formulation containing 100% of the biosourced polyol of the invention. That is, the exothermicity of the polyaddition reaction is different and results in lower activity of the catalysts.

The activation of these catalysts is at the origin of the rapidity of formation of the polyurethane network, and at the origin of the reaction for the formation of the triisocyanuric rings.

Surprisingly, the 35/65 formulation has a 48 seconds shorter tack-free time than the reference. This means that the 35 parts of PS 2412 are enough to maintain the activation of the traditional catalyst game. Also, the superior and unconventional functionality of the BASAB for a PUIR formulation makes it possible to reach the characteristic tack-free time the foam more quickly.

Two identical formulations to the control were prepared by replacing the PS 2412 reference polyol with BASAB. Foams could be obtained with good characteristics for the 35/65 foam. Nevertheless, during a total replacement, the 0/100 foams obtained have characteristic relatively slow measured foaming times.

Indeed, better results are obtained by using a combination of a co-polyol with BASAB. Ethylene glycol (EG) was preferred because being a short diol, it was very reactive, to promote initiation of the first exothermic reaction and increase the reaction between BASAB and polyisocyanate molecules. After different BASAB/EG ratio tests, the 85/15 wt % ratio showed the best result in the PUIR foam formulation.

Two catalysts were compared: potassium octoate (Ko) and potassium carboxylate (Pc). This last smaller catalyst, has a greater mobility and therefore a greater activity in the medium. The resulting optimized formulations, namely a B1-K0 formulation comprising 100% of biosourced polyester polyol (85 parts of BASAB and 15 parts of ethylene glycol) and potassium octoate (Ko) and a B2-PC formulation comprising 100% of biosourced polyester polyol (85 parts of BASAB and 15 parts of ethylene glycol and potassium carboxylate (Pc) are detailed in Table 3. The reference formulation (100/0) comprises 100% petrosourced polyester polyol (PS 2412) and potassium octoate (Ko).

TABLE 3

Catalyst ratio and Characteristic Times of the Different PUIR Foams

|  |  | Reference (100/0) | 35/65 | 0/100 | B1-K0 | B2-PC |
|---|---|---|---|---|---|---|
| Formulation | PS 2412 | 100$^a$ | 35 | 0 | 0$^a$ | 0$^a$ |
|  | BASAB | 0$^a$ | 65 | 100 | 85$^a$ | 85 |
|  | EG | 0$^a$ | 0 | 0 | 15$^a$ | 15$^a$ |
|  | Ko | 0.12$^b$ | 0.12$^b$ | 0.12$^b$ | 0.17$^b$ | 0$^b$ |
|  | N205 | 0.03$^b$ | 0.03$^b$ | 0.03$^b$ | 0.08$^b$ | 0.22$^b$ |
|  | Tegoamine C41 | 0.08$^b$ | 0.08$^b$ | 0.08$^b$ | 0.21$^b$ | 0.11$^b$ |
|  | Pc | 0$^b$ | 0$^b$ | 0$^b$ | 0$^b$ | 0.97$^b$ |
| Caracteristic times | Cream time (s) | 10 | 19 | 24 | 12 | 11 |
|  | String time (s) | 60 | 76 | n.m | 134 | 82 |
|  | Tack-free time (s) | 148 | 100 | ≥300 | 166 | 120 |

$^a$expressed as a number of parts with respect to the final product,
$^b$expressed as a percentage relative to the final product,
n.m: not measurable.

The B1-K0 formulation catalyzed with the same catalyst as the reference but in greater amount has a cream time relatively similar to the latter (Table 3). However, B1-K0 has a string time that has a delay of 74 seconds compared to the reference time and a delay of 18 seconds for the tack-free time. It is evidenced from these results that the formulation B1-K0 has distinct characteristics in terms of characteristic times compared to the reference. These differences, in particular the lengthening of the characteristic times, are an advantage to the formulation of rigid rigid PUIR foam produced in molds.

On the other hand, compared to the reference, the biosourced B2-PC formulation has a catalyst different from that of the reference. It is observed that the cream time of this formulation as well as the string times are closer to the times of the reference formulation, whereas the B2-PC tack-free time is 28 seconds faster than that of the reference. It is evidenced from these results that the B2-PC formulation has distinct characteristics in terms of characteristic time compared to B1-K0. This formulation having shorter characteristic times and similar to those of the reference is an advantage for the in-line production processes of rigid PUIR foam insulation board.

Beyond the characteristic times, the most important difference between these formulations is macroscopic.

Indeed, the characteristics of the foams of the previous formulations have been compared. It appears that the B2-PC foam has a clean surface, with a smooth outer skin, similar to the reference, while B1-K0 has an irregular surface (FIGS. 3, b and c) (presence of cracks and bubbles).

The main hypothesis justifying these surface differences between the B1-K0 foam on the one hand and the B2-PC and reference foams on the other hand is based on the differences in string time. Indeed, the string time of 134 s of B1-K0 is longer than that of B2-PC which is 82 s.

Since the B1-K0 and B2-PC formulations contain the same polymer, the longer string time reflects a longer time to reach the same degree of polymerization and therefore instability or fragility of the material during this step of polymerization. This fragility causes the cell walls to collapse under the pressure of the expanding gas generating visible cracks and bubbles on the surface of the foam. This takes place before the curing of the foam and the end of the polymerization, ie before the end of the foaming process.

Figure 2:
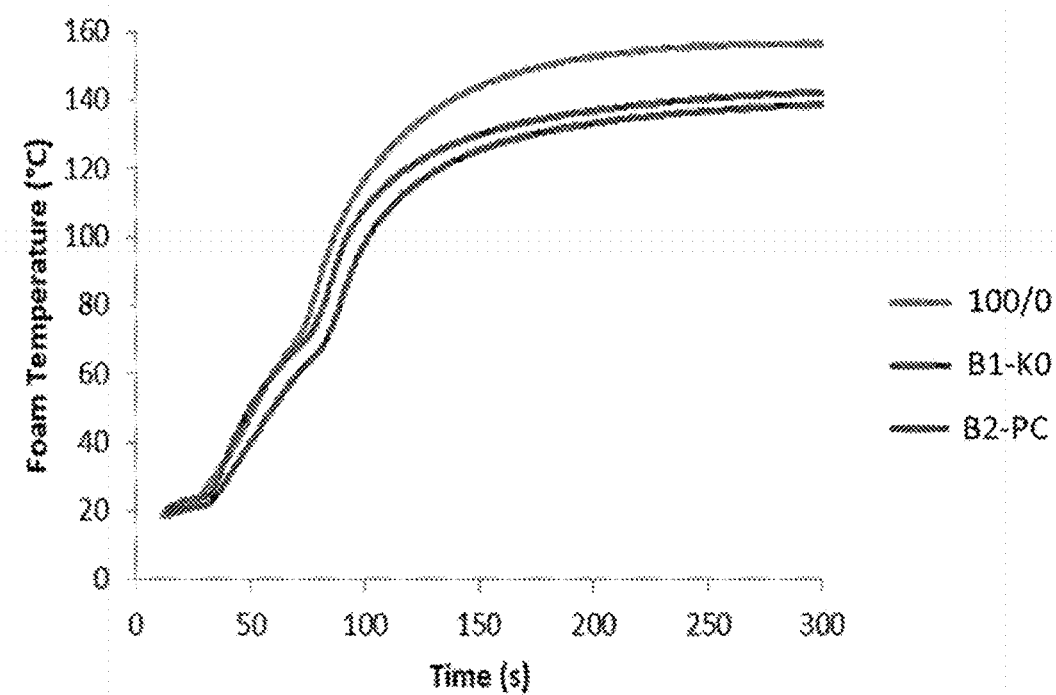
FIG. 2: Evolution of the temperature of the reaction medium during the foaming of the reference and of the two biosourced foams B1-K0 and B2-PC.

The evolution of the internal temperature of the foams during the foaming process was evaluated (FIG. 2). It is clear that the B1-PC foam rises more quickly than the B1-K0 foam. This reflects a greater reactivity of the reaction medium, certainly due to the choice of catalysts. In addition, the B1-K0 sample has a lower foaming temperature in all respects to the other two foams presented. The foaming temperature curve of B1-PC has a profile similar to that of the reference until the characteristic inflection thereof corresponding to the trimerization of isocyanates.

Finally, it can be seen that the overall kinetics of the PUIR foam of B2-PC is very close to the reference foam and the temperature of the foam is 140° C., which is similar to the foaming temperature of the petroleum-sourced reference.

The best foaming reactivity and therefore the best foaming kinetics, was obtained by increasing the foaming temperature (in particular by the catalyst change), by increasing the amount of BASAB in the mixture and by the addition of a co-polyol.

Thus, these results demonstrate that a PUIR foam formulation comprising biosourced polyol polyesters and having characteristics comparable to those of a petroleum-based polyester polyol formulation can be obtained. Such a formulation is particularly advantageous for rapid continuous in-line production of foam blocks or panels. On the other hand, these results also reveal that other types of PUIR formulations comprising biosourced polyol polyesters having foaming characteristics slower than the reference based on polyesters polyesters petroleum-based can also be obtained. Such formulations represent an advantage for the production of molded block foam. The bio-based polyester polyol (BASAB) is particularly advantageous in that it offers the opportunity to adapt the foaming characteristics or the kinetics of the foam according to the desired applications or manufacturing processes.

c. Closed Cell Percentage and Foam Morphology

Figure 4:
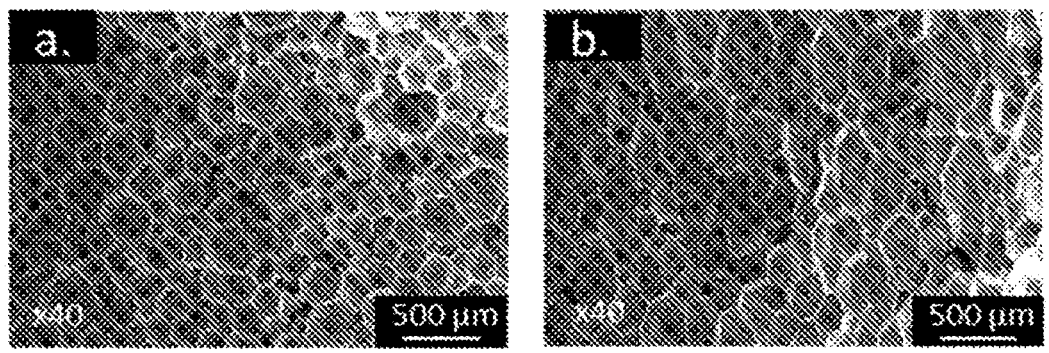
FIG. 4a: SEM images of the PUIR 100/0 foam: in the direction transverse to the expansion of the foam.
FIG. 4b: SEM images of the PUIR 100/0 foam: in the longitudinal direction at the expansion of the foam.

The morphologies of the foams obtained were compared by SEM. FIG. 4 shows the SEM images of samples of the reference PUIR foam cut in the transverse and longitudinal direction at the rise of the foam after foaming A typical alveolar structure in the transverse direction is clearly observed. Stretching of the cell in the longitudinal direction is characteristic of a partially free foaming process performed in an open cylindrical container (M. C. Hawkins, J. Cell. Plast., 2005, 41, 267-285). The SEM observations allowed the measurement of the anisotropic coefficients R of PUIR foams: 100/0, 35/65, 0/100, B1-K0 B2-PC studied (Table 4).

The anisotropic coefficients (R) reflect the shape of the cells of a foam. The coefficient R is the ratio of the two maximum measurable diameters in a cell. Thus a perfectly round cell will have a coefficient R equal to 1 (all diameters are identical in a circle). In contrast, a stretched cell of oval shape will have a coefficient R greater than 1. In this study the coefficients R are determined in two different planes. This makes it possible to evaluate the shape of the cells in a transversal section to the direction of expansion of the PUIR foams and similarly in the longitudinal direction to the expansion of the PUIR foams.

It is observed that for the R coefficients of the formulations 100/0, B1-K0 and B2-PC are close to 1.8 in the longitudinal direction. This means an oval shape of the cells of the foam. In the direction transverse to the rising of the foam, the calculated coefficient R is closer to 1.2. It reflects here a form of cells closer to the spherical shape. The formulations 35/65 and 0/100 have coefficients R less comparable. The wide distribution of cell sizes of these foams which results in large standard deviations of all their Feret diameters in the longitudinal and transverse directions results in cells of very anisotropic shape.

Comparing the reference foam with 34/65 and 0/100 foams, the latter have cells approximately 2 to 4 times larger than the reference based on 100% petrol-based polyol in all directions of study. The size of the cells is an impacting criterion for the final properties of a PUIR foam. For example, large cells generate poorer thermal insulation properties.

Comparing the reference foam with PUIR B1-K0 and B2-PC biosourced foams, the latter have cells of sizes almost similar to those of the reference in all directions (Table 4). Compared to the 35/65 and 0/100 formulations, their cell sizes are significantly smaller. This major gain on biosourced formulations is an advantage for their use in the field of thermal insulation of the building for example.

TABLE 4

Feret's diameter and anisotropy coefficient (R) of all foams PUIR in the longitudinal and transverse directions in the direction of foaming

| | | 100/0 | 35-65 | 0/100 | B1-K0 | B2-PC |
|---|---|---|---|---|---|---|
| Longitudinal direction | Feret max, $D_F^{max}$ (μm) | 408 ± 117 | 643 ± 189 | 860 ± 170 | 524 ± 215 | 521 ± 123 |
| | Feret min, $D_F^{min}$ (μm) | 223 ± 44 | 518 ± 147 | 550 ± 130 | 295 ± 112 | 298 ± 67 |
| | $D_F^{max}/D_F^{min}$ | 1.83 | 1.25 | 1.56 | 1.78 | 1.75 |
| Traversal direction | Feret max, $D_F^{max}$ (μm) | 275 ± 72 | 940 ± 260 | 1240 ± 380 | 386 ± 123 | 448 ± 122 |
| | Feret min, $D_F^{min}$ (μm) | 242 ± 72 | 420 ± 90 | 990 ± 300 | 324 ± 116 | 347 ± 122 |
| | $D_F^{max}/D_F^{min}$ | 1.14 | 2.24 | 1.25 | 1.19 | 1.29 |

The study of the previous kinetic foaming profiles has shown that the temperatures reached by the reaction medium during the foaming process are lower for the B1-K0 and B2-PC foams. These low temperatures are responsible for a delay before the trimerization of the isocyanates, causing lower reaction rates (longer string time). The increase in string time induces an increase in the coalescence process of the gas bubbles before complete polymerization of the polyurethane and polyisocyanurate network of the foam, which explains the observation of larger cell sizes for biosourced foams.

d. Foam Properties: Density, Closed Cell Rates and Chemical Composition (FT-IR)

TABLE 5

PUIR foam properties.

|  | 100/0 | 35-65 | 0/100 | B1-K0 | B2-PC |
|---|---|---|---|---|---|
| Bulk Density (kg/m$^3$) | 31.1 | 39.8 | n.d | 33.8 ± 2 | 32.8 ± 0.8 |
| Closed-cells percentage (%) | 95 | <50 | <50 | 86 | 85 | n.d: not determined

The apparent density of the foams shown in Table 5 is similar for all PUIR formulations, and is between 31 and 40 kg/m$^3$. The 35/65 foam has the highest apparent density (39.8 kg/m$^3$) and it is also the foam that has the lowest foaming temperature. The low foaming temperature limited the expansion of the swelling agent, resulting in a slightly more dense foam than the others. Foams B1-K0 and B2-PC, the optimized formulation does not have this characteristic since their density is closer to that of the reference.

Figure 5:
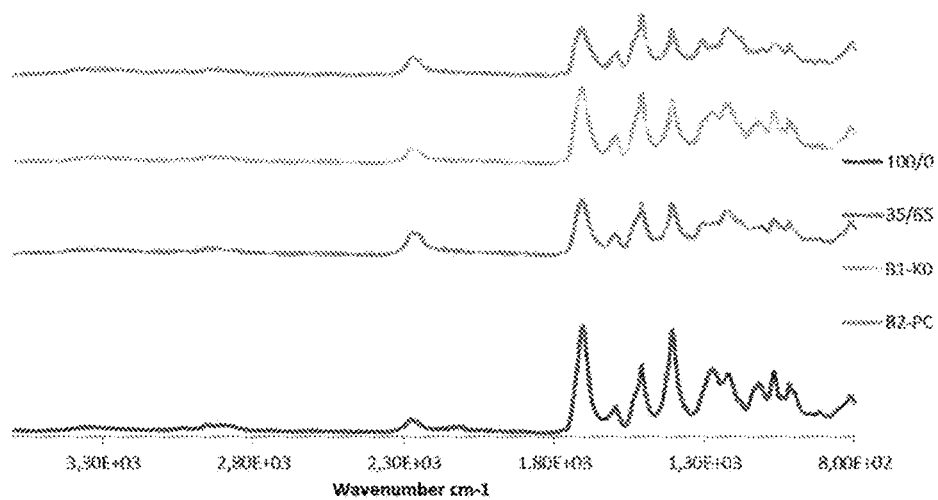
FIG. 5: FTIR spectrum of PUIR 100/0, 35/65, B1-K0 and B2-PC foams.

In order to confirm the chemical nature of the foams obtained, an infrared spectrometric (FT-IR) analysis was carried out. The FT-IR spectra of the formulated foams are shown in FIG. 5. All foams show characteristic peaks such as stretching stretching of NH groups at 3400-3200 cm$^{-1}$ and stretching vibrations of the C=O bond present in urethane groups at 1705 cm$^{-1}$. Signals at 2955 cm$^{-1}$ and 2276 cm$^{-1}$ are respectively attributed to C—H bond stretching of the polyurethane backbone and unreacted residual NCO groups. The 1596 cm$^{-1}$ signal corresponds to Ar—H stretching in phenyl groups derived from the polymeric polyisocyanate. The bending signal of the N—H groups is located at 1509 cm$^{-1}$ and the C—O stretch at 1220 cm$^{-1}$. Then, a strong signal at 1408 cm$^{-1}$ is attributed to the presence of isocyanurate rings typical of the PUIR foam formulation.

It is therefore concluded that the foams obtained, and in particular the foams based on biosourced polyester polyol, have a similar chemical composition to that of the 100% petroleum-based polyester polyol based foam. This proves that the differences concerning the characteristic times or foaming temperatures previously observed did not prevent the good formation of a PUIR network in all the formulations.

e. Thermal Resistance of Foams

The thermal stability of the PUIR foam samples was investigated by thermogravimetric analysis of the ATG and DTGA curves of all PUIR foams (not shown). All PUIR foams have classic weight loss in two stages. PUIR B1-K0 and B2-PC foams have superior thermal stability compared to the reference. Table 6 shows the maximum temperatures of the curve derived from weight loss: $T_{degmax1}$ and $T_{degmax2}$. $T_{degmax1}$ is around 300° C. for the three foams. $T_{degmax2}$ is observed at a temperature of 523° C. for the reference while the B1-K0 and B1-PC foam has higher $T_{degmax2}$, respectively 538 and 534° C.

In addition, they have a shoulder of the DTGA curve at more than 600° C. The first $T_{degmax1}$ corresponds to the decomposition of the urethane bond. The mechanism of decomposition of the urethane linkage is generally described as simultaneous dissociation of isocyanate and alcohol, formation of a primary and secondary amine, and formation of olefins. The second $T_{degmax2}$ is more pronounced than the first $T_{degmax1}$ and is associated with double degradation of isocyanurate and cleavage of carbon-carbon bonds (J. E. Sheridan and C. A. Haines, J. Cell. Plast., 1971, 7, 135-139). The first weight loss is less important because there is an isocyanurate bond. Isocyanurates are thermally more stable than urethane due to the absence of labile hydrogen and thus the second weight loss is mainly caused by carbon-carbon cleavage (H. E. Reymore et al., J. Cell. Plast., 1975, 11, 328-344). In the specific case of B1-K0 and B2-PC, $T_{degmax2}$ is higher and is attributed to their higher concentration in BASAB compared to the reference. The higher OH value of BASAB compared to PS 2412 increases the formation of urethane linkages and cross-linking of the PUIR network (A. A. Septevani, et al Ind. Crops Prod., 2015, 66, 16-26; Javni, Z. S., et al., J. Appl. Polym. Sci., 2000, 77, 1723-1734) making it more resistant to thermal degradation.

Table 6 also shows two temperatures corresponding to 50% ($T_{deg50\%}$) and 100% ($T_{deg100\%}$) weight loss of PUIR foams, respectively. $T_{deg50}$% and $T_{deg100}$%. The latter are similar between the reference foams and B1-K0. The B2-PC sample has a $T_{deg50\%}$ and a $T_{deg100\%}$ higher than those of the reference foam, which is in agreement with the previous observations. As a result, the B2-PC formulation makes it possible to obtain a foam that is more resistant to temperature than the reference foam based on petroleum-based polyester polyol.

TABLE 6

Degradation at 95% and 50% weight loss of PUIR foams samples

| Sample | ATG | | DTG | |
|---|---|---|---|---|
|  | $T_{deg50\%}$ (° C.) | $T_{deg100\%}$ (° C.) | $T_{deg50\%}$ (° C.) | $T_{deg100\%}$ (° C.) |
| 0% (Reference) | 448 | 645 | 301 | 523 |
| B1-K0-PC | 458 | 632 | 300 | 538 |
| B2-PC | 499 | 690 | 295 | 534 |

Closed cell PUIR foams based on the total substitution of a petroleum-sourced polyester polyol by the biosourced polyester polyol have been successfully prepared. The optimization of the formulation allowed to obtain a kinetics of foaming similar to that of the reference petroleum-sourced. The study was conducted using two different catalysts. PUIR foams have a high content of closed cells which is very interesting for meeting thermal insulation characteristics. Finally, the most striking point concerns PUIR biosourced foams which has a higher stability to thermal degradation than the petroleum-sourced reference.

The invention claimed is:

1. A rigid foam or a composition allowing a rigid foam to be obtained comprising a polyester polyol or a polymer comprising a polyester polyol, wherein said polyester polyol has the general formula Rx-Ry-Rz-Ry'-Rx' wherein Rz is a C4 to C7 sugar alcohol, Ry and Ry' are identical or different diesters having formula —OOC—$C_n$—COO— with n between 2 and 10, and Rx and Rx' are identical or different C2 to C8 monoalcohols.

2. The rigid foam or composition allowing a rigid foam to be obtained according to claim 1, wherein the sugar alcohol Rz is chosen from sorbitol, erythritol, xylitol, arabitol, ribitol, dulcitol, mannitol and volemitol.

3. The rigid foam or composition allowing a rigid foam to be obtained according to claim 1, comprising at least one reaction catalyst, at least one swelling agent, a stabilizer, at least one polyisocyanate having a functionality at least equal to 2, and, optionally, at least one co-polyol.

4. The rigid foam or composition allowing a rigid foam to be obtained according to claim 1, comprising at least one C2 to C8 co-polyol.

5. The rigid foam or composition allowing a rigid foam to be obtained according to claim 4, having a polyester polyol/co-polyol(s) ratio from 70/30 to 99/1.

6. The rigid foam or composition allowing a rigid foam to be obtained according to claim 4, wherein the at least one copolyol is chosen from ethylene glycol, glycerol, 1,4-butanediol, butane-1,3-diol, 1,3-propanediol, propane-1,2-diol, 1,5-pentanediol, 1,6-hexanediol, 1,2-propylene glycol, 3-oxapentane-1,5-diol, 2-[2-(2-hydroxyethoxy)ethoxy]ethanol, benzene-1,2,4-triol, benzene 1,2,3-triol, benzene 1,3,5-triol, sorbitol, erythritol, xylitol, araditol, ribitol, dulcitol, mannitol and volemitol.

7. A panel or a block of rigid foam comprising the rigid foam according to claim 1.

8. A method for thermal, sound, or cryogenic insulation or a method for filling, water-proofing, sealing or improving the buoyancy of a vessel or of an object by the deposition or the introduction of blocks or of panels of rigid foam comprising the rigid foam according to claim 1 or by spraying said rigid foam or of a composition allowing said rigid foam to be obtained.

9. The rigid foam or composition allowing a rigid foam to be obtained according to claim 1, wherein Rz is a C5 or C6 sugar alcohol.

10. The rigid foam or composition allowing a rigid foam to be obtained according to claim 1, wherein n is between 3 and 10.

11. The rigid foam or composition allowing a rigid foam to be obtained according to claim 1, wherein n is between 4 and 10.

12. The rigid foam or composition allowing a rigid foam to be obtained according to claim 1, wherein Rx and Rx' are C3 to C8 monoalcohols.

13. The rigid foam or composition allowing a rigid foam to be obtained according to claim 1, wherein Rx and Rx' are C4 monoalcohols.

14. The rigid foam or composition allowing a rigid foam to be obtained according to claim 1, comprising:
at least 1 to 100 parts of the polyester polyol,
0 to 70 parts of at least one copolyol,
150 to 500 parts of a polyisocyanate,
0.5 to 5 parts of a catalyst,
0.5 to 15 parts of a swelling agent,
0 to 5 parts of a stabiliser, and
0 to 20 parts of a flame retardant.

15. The rigid foam or composition allowing a rigid foam to be obtained according to claim 14, wherein the catalyst is an amine catalyst.

16. The rigid foam or composition allowing a rigid foam to be obtained according to claim 1, comprising:
at least 1 to 100 parts of the polyester polyol,
from 1 to 50 parts of at least one copolyol,
150 to 500 parts of a polyisocyanate,
0.5 to 5 parts of a catalyst,
0.5 to 12 parts of a swelling agent,
0 to 5 parts of a stabiliser, and
0 to 20 parts of a flame retardant.

17. The rigid foam or composition allowing a rigid foam to be obtained according to claim 1, further comprising 0.5 to 12 parts of a chemical swelling agent and 0 to 60 parts of a physical swelling agent.

18. The rigid foam or composition allowing a rigid foam to be obtained according to claim 4, having a polyester polyol/co-polyol(s) ratio from 75/25 to 95/5.

* * * * *